United States Patent
Chung

(10) Patent No.: US 11,413,252 B2
(45) Date of Patent: Aug. 16, 2022

(54) MEMBRANE LIPID COATED VIRAL NANOPARTICLES AND METHOD OF USE

(71) Applicant: Coastar Therapeutics Inc., San Diego, CA (US)

(72) Inventor: Eddie Yocon Chung, San Diego, CA (US)

(73) Assignee: Coastar Therapeutics Inc., San Diego, CA (US)

(*) Notice: Subject to any disclaimer, the term of this patent is extended or adjusted under 35 U.S.C. 154(b) by 109 days.

(21) Appl. No.: 16/606,754

(22) PCT Filed: Apr. 21, 2018

(86) PCT No.: PCT/US2018/028752
§ 371 (c)(1),
(2) Date: Oct. 20, 2019

(87) PCT Pub. No.: WO2018/195526
PCT Pub. Date: Oct. 25, 2018

(65) Prior Publication Data
US 2020/0060979 A1 Feb. 27, 2020

Related U.S. Application Data

(60) Provisional application No. 62/488,685, filed on Apr. 21, 2017.

(51) Int. Cl.
| | |
|---|---|
| A61K 9/50 | (2006.01) |
| A61K 35/761 | (2015.01) |
| C12N 7/00 | (2006.01) |
| A61K 9/00 | (2006.01) |
| A61K 9/51 | (2006.01) |

(52) U.S. Cl.
CPC .......... *A61K 9/5068* (2013.01); *A61K 9/0019* (2013.01); *A61K 9/5184* (2013.01); *A61K 9/5192* (2013.01); *A61K 35/761* (2013.01); *C12N 7/00* (2013.01); *C12N 2710/10332* (2013.01)

(58) Field of Classification Search
None
See application file for complete search history.

(56) References Cited

U.S. PATENT DOCUMENTS

| | | | | |
|---|---|---|---|---|
| 5,879,675 | A * | 3/1999 | Galili | ............ A61P 31/00 424/93.1 |
| 2010/0203024 | A1 | 8/2010 | Terman et al. | |
| 2014/0335115 | A1 | 11/2014 | Alzhanova et al. | |
| 2015/0284691 | A1 | 10/2015 | Kummel et al. | |
| 2016/0067191 | A1 * | 3/2016 | Ortac | ............ A61P 35/00 424/490 |
| 2016/0317591 | A1 | 11/2016 | Aboody et al. | |

FOREIGN PATENT DOCUMENTS

| | | |
|---|---|---|
| JP | 2016520567 A | 7/2016 |
| WO | WO2006/090816 | 8/2006 |
| WO | WO2014172685 | 10/2014 |
| WO | WO 2016/010840 A1 | 1/2016 |
| WO | WO2016/192451 | 12/2016 |
| WO | WO 2016/205009 A1 | 12/2016 |

OTHER PUBLICATIONS

Correa at al. "Highly scalable, closed-loop synthesis of drug-loaded, layer-by-layer nanoparticles," Advanced Functional Materials, Feb. 16, 2016, 26 (7), 991-1003.
Matthias Duebgen et al.: "Stem Cells Loaded With Multimechanistic Oncolytic Herpes Simplex Virus Variants for Brain Tumor Therapy", Journal of the National Cancer Institute, vol. 106, No. 6, May 16, 2014, 1-9.
Komarova Svetlana et al.: "Mesenchymal progenitor cells as cellular vehicles for delivery of oncolytic adenoviruses", Molecular Cancer Therapeutics, American Association for Cancer Research, vol. 5, No. 3, Mar. 1, 2006, 755-766.
The extended European search Report in corresponding European Patent Application No. EP18787969.7, dated Aug. 6, 2020.

* cited by examiner

*Primary Examiner* — Nicole Kinsey White
(74) *Attorney, Agent, or Firm* — C. Jason Liang

(57) ABSTRACT

Disclosed is a nanoparticle comprising an inner core comprising a virus; and an outer surface comprising a cellular membrane derived from a cell, and process of making thereof. The virus is an oncolytic virus and cellular membrane is derived from for example red blood cells.

8 Claims, 6 Drawing Sheets

Virus detection assay

MEMBRANE LIPID COATED VIRAL NANOPARTICLES AND METHOD OF USE

CROSS REFERENCE

This application is the U.S. national phase of International Application No. PCT/US18/28752, filed Apr. 21, 2018, which claims the benefit of U.S. provisional application Ser. No. 62/488,685, filed Apr. 21, 2021, each of which is incorporated herein by reference in its entirety.

BACKGROUND OF THE INVENTION

Oncolytic viruses (OVs) are viruses that preferentially infect and kill cancer cells. The viruses grow and cause lysis (oncolysis) of cancer cells or trigger other mechanisms to disturb the cancer-immunosuppressive microenvironment and trigger the body's immune response to clear cancer cells. Recent successful clinical data and drug approvals have increased public attention on oncolytic virotherapy. The use of oncolytic virotherapy can be combined with other drugs, immune check point inhibitors, and T-cell therapy to improve outcomes for cancer patients.

Routes of delivery of OVs include intratumoral (i.t.) injection, intravenous (i.v.) delivery, and intra-peritoneal delivery, where intratumoral injection is applied mostly.

SUMMARY OF THE INVENTION

In accordance with the present invention, the present invention provides a process of making a particular nanoparticle comprising combining an inner core comprising a virus, or the like, and an outer surface comprising a cellular membrane derived from a cell in a non-salt water solution; applying sonication to said solution to form a nanoparticle comprising said inner core coated with said outer surface.

In one aspect, provided herein are nanoparticles comprising an inner core comprising a virus; and an outer surface comprising a cellular membrane derived from a cell.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

Figure 1:
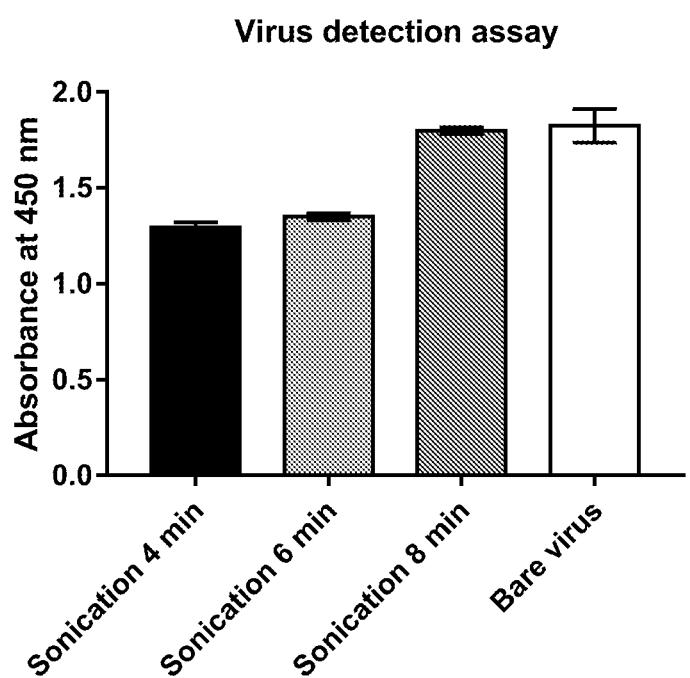
FIG. 1 shows the exemplary results of the virus detection assay of different sample batches prepared by applying various sonication times of 4 minutes, 6 minutes, 8 minutes, respectively vs. bare virus.

FIG. 4 shows the sizes of bare virus and coated virus measured by dynamic light scattering.

FIG. 5 shows an exemplary virus detection assay result indicating the virus was coated resulted a very low absorbance at 450 nm vs. one of the bare virus showing much higher absorbance.

FIG. 6 provides a follow up virus detection assay after the coated virus nanoparticles went through a de-coating process resulted in a bare virus in comparison with the coated virus.

DETAILED DESCRIPTION OF THE INVENTION

Currently, most oncolytic virus therapies are limited to local regional injection (such as intratumoral, i.t.), and whether a single injection is enough to achieve therapeutic effect is still under investigation. Also, some OVs have been shown to have an acute, transient toxicity profile, and thus injecting the virus may induce a competitive immune response against the virus rather than against the tumor cells. Also, there is a problem for intravenous delivery of OVs where OVs may be cleared rapidly from the bloodstream, thus requiring frequent or high-dose administrations, leading to increased therapy costs and potential safety issues. Therefore, it is needed to provide a composition comprising OVs that can be administered and remain in circulation for extended periods of time for ultimate delivery of therapeutic agents to targeted cells.

It is known in the art that to achieve stealth moiety on nanoparticle, the adoption of polyethylene glycol (PEG) is employed. However, an anti-PEG immunological response may be triggered and thus such approach is problematic. Alternative approaches such as utilizing zwitterionic materials (e.g., poly(carboxybetaine) and poly(sulfobetaine)) have been proposed.

Recently, a top-down biomimetic approach to provide functionalized nanoparticles by coating with natural erythrocyte membranes, including both membrane lipids and associated membrane proteins was realized, providing long-circulating cargo delivery. See C-M. J. Hu et al., "Erythrocyte membrane-camouflaged polymeric nanoparticles as a biomimetic delivery platform," Proc. Natl. Acad. Sci. USA 2011, July 5; 108(27): 10980-10985. Particularly, the membrane lipids derived from a blood cell (e.g., red blood cell (RBC), white blood cell (WBC), or platelet) are of particular interests to coat various of materials but not the oncolytic viruses, or the like.

Various attempts to prepare nanoparticles with RBC coated oncolytic viruses were tried but not successful following the known methods. It is the first time that an oncolytic virus, or the like has been coated with RBC membrane. In accordance with the practice of the invention, it is surprisingly found that a certain condition must be employed to prepare invention nanoparticles disclosed herein.

The term "oncolytic virus" referred herein includes non-limited examples of herpesvirus; vaccinia virus; reovirus; adenovirus; measles virus, parvovirus, or combinations thereof.

It is known in the art that viruses can be used as vectors for delivery of suicide genes, encoding enzymes that can metabolize a separately administered non-toxic pro-drug into a potent cytotoxin, which can diffuse to and kill neighboring cells. Thus, the therapeutic agent disclosed here also includes such vectors, suicide genes, or encoding enzymes.

In accordance with the present invention, it is found surprising a process to make a nanoparticle comprising combining an inner core comprising a virus (a therapeutic agent), and an outer surface comprising a cellular membrane derived from a cell in a non-salt water solution; applying sonication to said solution to form a nanoparticle comprising said inner core coated with said outer surface. Contrary to the known methods that a salt solution such as saline and PBS solution is needed in the cellular membrane coating of the inner core process, a non-salt water solution (e.g., a sugar containing solution), or the like (such as a component with similar property of a sugar in water solution), is required for coating a virus, such as an oncolytic virus. For the first time a nanoparticle comprising an inner core comprising a virus; and an outer surface comprising a cellular membrane derived from a cell is prepared in accordance with the practice of this invention. It is surprising found that a 5% to 15%, a 7% to 14%, a 9% to 11% of a non-salt water solution (such as a sugar containing solution) used in the process of preparing nanoparticles comprising a core of a virus, or the like, is needed. In some embodiments, a non-salt water solution (such as a sugar containing solution) of 5%, 6%, 7%, 8%, 9%, 10%, 11%, 12%, 13%, 14%, or 15% is needed in the process of making nanoparticles comprising a core of a virus, or the like.

In some embodiments provide a nanoparticle comprising an inner core comprising a virus; and an outer surface comprising a cellular membrane derived from a cell. In certain embodiments, said virus is an oncolytic virus. In certain embodiments, said oncolytic virus is herpesvirus; vaccinia virus; reovirus; adenovirus; measles virus, parvovirus, or combinations thereof. In certain embodiments, said virus is adenovirus.

In some embodiments, said cell is a blood cell, an adipocyte, a stem cell, an endothelial cell, an exosome, a secretory vesicle or a synaptic vesicle. In certain embodiments, said blood cell is red blood cell, white blood cell, or platelet. In certain embodiments, said blood cell is red blood cell.

In some embodiments provide a process of making a nanoparticle comprising combining an inner core comprising a virus, and an outer surface comprising a cellular membrane derived from a cell in a non-salt water solution; applying sonication to said solution to form a nanoparticle comprising said inner core coated with said outer surface. In certain embodiments, said non-salt water solution comprises sugar, or the like (such as a component with similar property of a sugar in water solution). In certain embodiments, said non-salt water solution is a sugar solution. In certain embodiments, said sugar solution is sucrose, or dextrose containing solution. In some embodiments, said virus is an oncolytic virus. In certain embodiments, said oncolytic virus is herpesvirus; vaccinia virus; reovirus; adenovirus; measles virus, parvovirus, or combinations thereof. In certain embodiments, said oncolytic virus is adenovirus. In some embodiments, said cell is a blood cell, an adipocyte, a stem cell, an endothelial cell, an exosome, a secretory vesicle or a synaptic vesicle. In certain embodiments, said blood cell is red blood cell, white blood cell, or platelet. In certain embodiments, said blood cell is red blood cell.

The invention provides a cellular membrane derived nanoparticle for delivering of a therapeutic agent, such as an oncolytic virus. The agent is essentially camouflaged by coating the therapeutic agent such as oncolytic virus with cellular membrane lipids.

In some embodiments, a therapeutic agent such as oncolytic virus is coated with lipids compatible with circulation within the bloodstream of a subject (e.g., a patient). This allows delivery of the agent to tumor vasculature via the EPR (enhanced permeability and retention) effect, where certain molecules tend to accumulate in tumor tissues more than in normal tissues. The EPR effect is usually employed to describe nanoparticle and liposome delivery to cancer tissue. One of many examples is the work regarding thermal ablation with gold nanoparticles. Thus, in some embodiments, the nanoparticles disclosed herein would accumulate near a tumor's vasculature, and the therapeutic agents (e.g., a OV) will come into contact with cancer cells. The OV then infects the cell, resulting in cell lysis, death, or removal.

In some embodiments, provided herein are nanoparticles comprising an inner core comprising an oncolytic virus, and the like; and an outer surface comprising a cellular membrane derived from a cell such as a blood cell (e.g., red blood cell (RBC or erythrocyte), white blood cell, or platelet), an adipocyte, a stem cell, an endothelial cell, or the like. In certain embodiments, the cellular membrane is derived from a blood cell such as red blood cell.

In some embodiments provide the method to prepare the nanoparticles disclosed herein. For example, blood cells can be purified from whole blood or from processed red blood cells obtained from a blood supplier. RBCs are particularly useful as a membrane source because of their abundance in human blood and the ease of collecting blood from individual donors. RBCs can be provided in the form of erythrocyte ghosts (or RBC ghosts), where the internal proteins have been depleted, leaving the membrane components essentially intact. The use of RBC ghosts also reduces the presence of RBC cellular proteins that may interfere during the coating process. In some embodiments, the RBC is a type O-negative blood cell (i.e., an "universal donor"). Such membrane source can be used in the preparation of the nanoparticles to deliver the therapeutic agent (e.g., an OV) to a greater number of subjects. In certain embodiments, one can use cell membranes derived from the same patient for personalized batches of nanoparticles.

Compared to other platforms, for example a PEG coating nanoparticle, the RBC membrane derived nanoparticle has many surface markers such as CD47, CD59 (MAC-inhibitory protein, avoiding complement cell lysis), CD55 (DAF), CD35 (CR1) and other members in immunoglobulin superfamily to protect itself from body clearance. In some embodiments, the cell membrane used for coating herein can further incorporate non-lipid components, such as cell surface markers, MEW molecules, and glycoproteins. In other embodiments, the cell membrane can further incorporate hydrophilic components, such as PEG.

The term "cellular membrane" as used herein refers to a biological membrane enclosing or separating structure acting as a selective barrier, within or around a cell or an emergent viral particle. The cellular membrane is selectively permeable to ions and organic molecules and controls the movement of substances in and out of cells. The cellular membrane comprises a phospholipid uni- or bilayer, and optionally associated proteins and carbohydrates. As used herein, the cellular membrane refers to a membrane obtained from a naturally occurring biological membrane of a cell or cellular organelles, or one derived therefrom.

As used herein, the term "naturally occurring" refers to one existing in nature.

As used herein, the term "derived therefrom" refers to any subsequent modification of the natural membrane, such as isolating the cellular membrane, creating portions or fragments of the membrane, removing and/or adding certain components, such as lipid, protein or carbohydrates, from or into the membrane taken from a cell or a cellular organelle. A membrane can be derived from a naturally occurring membrane by any suitable methods. For example, a membrane can be prepared or isolated from a cell and the prepared or isolated membrane can be combined with other substances or materials to form a derived membrane. In another example, a cell can be recombinantly engineered to produce "non-natural" or "natural" substances that are incorporated into its membrane in vivo, and the cellular or viral membrane can be prepared or isolated from the cell to form a derived membrane.

A cellular membrane can be prepared by known methods. For example, cells can be broken using a microfluidizer (MF), or a hypotonic solution, such as water, followed by ultrafiltration or diafiltration with saline or PBS. In some cases, a solution with higher ionic strength has been useful for removing blood from pork liver, so a PBS or NaCl solution can help remove intracellular mass through the filtration process. An anticoagulant, such as EDTA, can also be used, for example during diafiltration to remove impurities. In some embodiments, a Tangential Flow Filtration (TFF) device or centrifugation can be used to purify the membranes. The purified membrane components can be tested for the presence of cellular proteins, such as by a BCA protein test. Preferably, most non-membrane components are removed prior to coating.

Despite the much efforts, it was found that following the known methods, such as the procedures in US2013/0337066, a virus such as an oncolytic virus or a CRISPR, a DNA sequence from viruses, cannot be coated or encapsulated by a cell membrane (e.g., a RBC membrane). It is surprisingly found that the cell membranes (e.g., RBC ghosts) coat the virus, or the like, only in certain conditions. The process to prepare the nanoparticles disclosed herein requires (1) sonication of the mixture of RBC ghosts and OVs in (2) non-salt solution such as a sucrose solution.

In accordance with the practice of the invention, viruses suitable for coating include oncolytic viruses as well as other viruses that can infect a cancer cell. Viruses can have enveloped or noneveloped forms. In some embodiments, viral vectors are preferred because they can infect a cancer cell and replicate (replication competency).

Certain Pharmaceutical and Medical Terminology

The term "acceptable" with respect to a formulation, composition or ingredient, as used herein, means having no persistent detrimental effect on the general health of the subject being treated.

The term "carrier," as used herein, refers to relatively nontoxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical composition" refers to a mixture of a nanoparticle (i.e., nanoparticle described herein) with other chemical components, such as, disintegrators, binders, lubricants, carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

All of the various embodiments or options described herein can be combined in any and all variations. The following Examples serve only to illustrate the invention and are not to be construed in any way to limit the invention.

EXAMPLES

Example 1. Exemplary Preparation of Cell Membrane Preparation

The cell membrane preparation (e.g., a RBC ghost preparation) is known the art. Here a non-limited example of preparing a cell membrane, a RBC cell membrane, was followed to provide an exemplary cell membrane for invention nanoparticles preparation.

Equipment and Materials Requirement:

| Equipment/Accessories |
| --- |
| Millipore Labscale TFF System |
| Millipore Pellicon 2 mini TFF filter (PXDVPPC50) |
| 0.5 mM EDTA |
| DPBS (10X), no calcium, no magnesium |
| Packed RBC, ACD-A anticoagulant |

Procedure:
1. Place the packed red blood cell bags in −80° C. fridge and freeze overnight. Thaw packed red blood cell in 4° C. fridge in the next morning.
2. Pour 360 mL of 0.5 mM EDTA into the media bottle, store in fridge overnight.
3. Add 40 mL blood from pRBC to media bottle, shack to mix well. Gentle mix in the fridge for 30 min.
4. Place 400 mL WFI water into TFF (Millipore Labscale TFF System) process reservoir and close the reservoir. Start the TFF system, turn the flow rate knob to level 4. Recirculate the system for 5 min and push all the water through the permeate line to pre-wet the filter (Millipore Pellicon 2 mini TFF filter, PXDVPPC50). Pause the system.
5. Pour the mixture from step 3 into the TFF process reservoir.
6. Concentrate the mixture to 100 mL.
7. Diafiltration with 400 mL PBS. Slowly pour in the PBS into the reservoir to keep the solution in the reservoir 100±50 mL.
8. Diafiltration with 200 mL 0.5 mM EDTA. Slowly pour in the EDTA solution into the reservoir to keep the solution in the reservoir 100±50 mL.
9. Final concentration to 40 mL. Monitor the pressure, lower the pump speed to keep pressure <40 psi.
10. Pump out the lipid into a 50 mL conical tube, store in −80° C. freezer for further analysis to confirm preparation of cell membrane and/or processes.

Example 2: Failure Attempt to Prepare Nanoparticles Comprising a Virus Core Following Known Methods with Different Sonication Time Study This procedure is describing the lab scale process for 1 mL coated virus (10^10 VP/mL) using probe sonication. The excipient cell membrane (e.g., erythrocyte membrane) used in this process is equivalent to 0.1 mL of packed red blood cells as raw material. The following is a detailed description of attempting preparation of nanoparticles comprising a virus core following the known method.

Because the first few attempts to prepare nanoparticles comprising a core of a virus following the known methods such as one in US Publication No. 2013/0337066 were not successful, it was decided to explore the energy condition by applying different sonication time (4 minutes, 6 minutes, and 8 minutes), hoping to prepare nanoparticle comprising a core of an exemplary virus (i.e., human type 5 adenovirus).

Equipment and materials: the following is a brief description of the equipment and material used for synthesizing 1 mL coated virus:

Probe Sonicator: Qsonica XL2000

List of Raw Materials:

| Name | Description | Notes |
| --- | --- | --- |
| Adenovirus | Human type 5 adenovirus | From vector biolabs |
| Solution used in the mixture | Saline | As described in the known method |
| $H_2O$ | Sterile water for injection | |
| RBC membrane | Made from RBC Membrane Derivation Process as in Example 1 | 1.5 mg/mL based on BCA |

Procedure

1. Add 800 uL of saline in a 1.5 mL microcentrifuge tube.
2. Add 200 uL of RBC membrane (1.5 mg/mL) into the tube, mix well. This will make process mixture with 0.3 mg/mL membrane.
3. Turn on the power of probe sonicator, wipe the probe with 70% ethanol and move only the probe into the biohood.
4. Adjust the power of the sonicator to level 2 (output ~3 W)
5. Prepare an ice box with cold water to keep the process temperature at <4° C.
6. Add 10 uL adenovirus stock solution (Vector biolabs, Lot #20170922) into the process mixture.
7. Put the tube into the ice box. Dip the probe into the tube. Don't let the probe touch the bottom.
8. Manually sonicate the mixture with 1 second sonication and 1 second interval between each sonication. Maintain this step for 4, 6, and 8 min to produce three sample batches.
9. For the bare virus, follow steps 1~8, but change the solution in 2. to molecular grade water.
10. Follow vendor's procedure (Virusys Corporation, AK290-2) to obtain the sandwich ELISA data for each batch.

The coated virus nanoparticles were to be confirmed by the virus detection assay. The assay is a double antibody (sandwich) ELISA that utilizes a monoclonal anti-adenovirus antibody to capture the antigen from the sample. Following sample incubation, a biotinylated detection antibody is added and this step is followed by HRP-Streptavidin. The presence of hexon antigen is visualized by the addition of an HRP substrate followed by the addition of a stop reagent. The development of color within the well is indicative of the presence of adenovirus hexon antigen in the sample. For quantitative purposes, Virusys offers a separate calibration kit (AK291, Adenovirus Antigen Calibration Kit) which can be used in conjunction with this product to generate a standard curve for quantitative measurement.

The results show that applying 4 minutes of sonication time seems to provide a better result based on virus detection assay (See FIG. 1). However, when comparing the essay results between all batches and the control sample (i.e., a bare virus sample), absorbance difference is not big enough to warrant a successful coating of the virus. Thus, a change of other condition is needed.

Example 3. Failure Attempt to Prepare Nanoparticles Comprising a Virus Core Following Known Methods with High Shear Homogenizer Equipment and materials used are the same as in Example 2 except PBS solution was used for the mixture of RBC membrane with the virus stock solution. The mixture was then gone through high shear homogenizer process as detailed below.

Procedure:
1. Pour cold water into the cooling box of LM10 high shear homogenizer (Microfluidics). Connect the compressed air to the machine, adjust the air pressure to around 120 psi.
2. Fill the reservoir with 100 mL deionized water, set the processing pressure to 10 K psi. Wash the system with deionized water twice and PBS twice.
3. Mix 14 mL PBS with 1 mL cell lipid (1.5 mg/mL) and 50 uL adenovirus ($10^{12}$ vp/mL, Vector Biolabs), pour the mixture into the reservoir.
4. Start the machine, repeat the high shear stroke for 5 times.
5. Collect sample from the product container.

The experiment was not successful, no virus was detected using virus detection assay. The virus was potentially destroyed by the high shear force generated by the equipment. Thus, despite the successfully application of RBC membrane to a core comprising non virus materials, the condition leading to a successful nanoparticle comprising a core of an exemplary virus disclosed herein was still questionable.

Example 4: Attempts to Prepare Nanoparticles Comprising a Virus Core with the Change of Various of Mixture Solutions Based on the known method and scientific principles, a saline or PBS solution of RBC membrane coating or encapsulating process is needed since these solutions were used to prepare RBC ghosts. Contrary to the known procedure, a few non salt solutions were used to explore the "non-traditional" procedure.
1. Add 800 uL of various solution (e.g., saline, sucrose, dextrose, lysine-dextrose) in a 1.5 mL microcentrifuge tube.
2. Add 200 uL of RBC membrane (1.5 mg/mL) into the tube, mix well. This will make process mixture with 0.3 mg/mL membrane.
3. Turn on the power of probe sonicator, wipe the probe with 70% ethanol and move only the probe into the biohood.
4. Adjust the power of the sonicator to level 2 (output ~3 W)
5. Prepare an ice box with cold water to keep the process temperature at <4° C.
6. Add 10 uL adenovirus stock solution (Vector biolabs, Lot #20170721.2) into the process mixture.
7. Put the tube into the ice box. Dip the probe into the tube. Don't let the probe touch the bottom.
8. Manually sonicate the mixture with 1 second sonication and 1 second interval between each sonication. Maintain this step for 4 min to produce various of batches.
9. Follow vendor's procedure (Virusys Corporation, AK290-2) to obtain the sandwich ELISA data for confirmation and comparison of the prepared batches.

Figure 2:
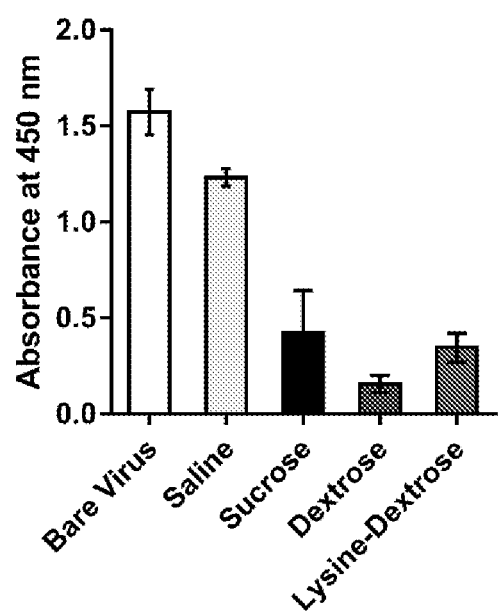
FIG. 2 shows the exemplary results of the virus detection assay of different sample batches prepared by combining RBC membrane with a core of a virus in various solutions in the nanoparticle preparation process. There are four sample batches (combining RBC membrane with the virus stock solution in saline, sucrose, dextrose, and lysine-dextrose solution, respectively) and one control batch (bare virus).

Based on the known procedure described in US 2013/033,7066, saline or PBS should be used to prepare nanoparticles. However, as clearly shown in FIG. 2, the saline batch yielded very poor results of encapsulated (or coated) nanoparticles as the ELISA assay showed almost the same absorbance in comparison with the uncoated virus (control). On the other hand, unexpectedly and surprisingly, the non-salt solution batches such as sugar containing solution batches (e.g., sucrose, dextrose, and lysine-dextrose) exhibit much lower absorbance indicating more and better coating of RBC membrane over the virus core.

Example 5: Coating of RBC-Membrane with an Oncolytic Virus Under an Exemplary Condition To verify the unexpectedly found results with the use of non-salt solution for the mixture of RBC membrane with the virus stock solution, an exemplary invention procedure as shown below was used to prepare nanoparticles comprising a virus core.

Equipment, materials are the same as ones in Example 2 except 11% of sucrose solution was used for the mixture of RBC membrane with the virus stock solution.

List of Raw Materials:

| Name | Description | Notes |
|---|---|---|
| Adenovirus | Human type 5 adenovirus | From vector biolabs |
| Sucrose | | For making 11% solution |
| H$_2$O | Sterile water for injection | |
| RBC membrane | Made from RBC Membrane Derivation Process as in Example 1 | 1.5 mg/mL based on BCA |

List of Buffers and Solutions:

| Name | Description | Quantity |
|---|---|---|
| Sucrose solution | 11% | 10 mL |
| Coating process mixture | 0.3 mg/mL membrane based on BCA | 1 mL |

Procedure:
1. Add 800 uL of 11% sucrose solution in a 1.5 mL microcentrifuge tube.
2. Add 200 uL of RBC membrane (1.5 mg/mL) into the tube, mix well. This makes process mixture with 0.3 mg/mL membrane.
3. Turn on the power of probe sonicator, wipe the probe with 70% ethanol and move only the probe into the biohood.
4. Adjust the power of the sonicator to level 2 (output ~3W)
5. Prepare an ice box with cold water to keep the process temperature at <4° C.
6. Add 2.5 uL exemplary oncolytic virus (e.g., adenovirus stock solution (Vector biolabs, Lot #20170721.2) into the process mixture, resulting about a 9% of sucrose solution of the mixture. It is expected by a skilled person in the art that 5% to 15% of sugar solution would work in the similar condition.
7. Put the tube into the ice box. Dip the probe into the tube. Don't let the probe touch the bottom.
8. Manually sonicate the mixture with 1 second sonication and 1 second interval between each sonication. Maintain this step for 4 min to prepare nanoparticles comprising a core of the virus.
9. For the bare virus, follow steps 1-9, but change the solution in 2. to molecular grade water.

Figure 3:
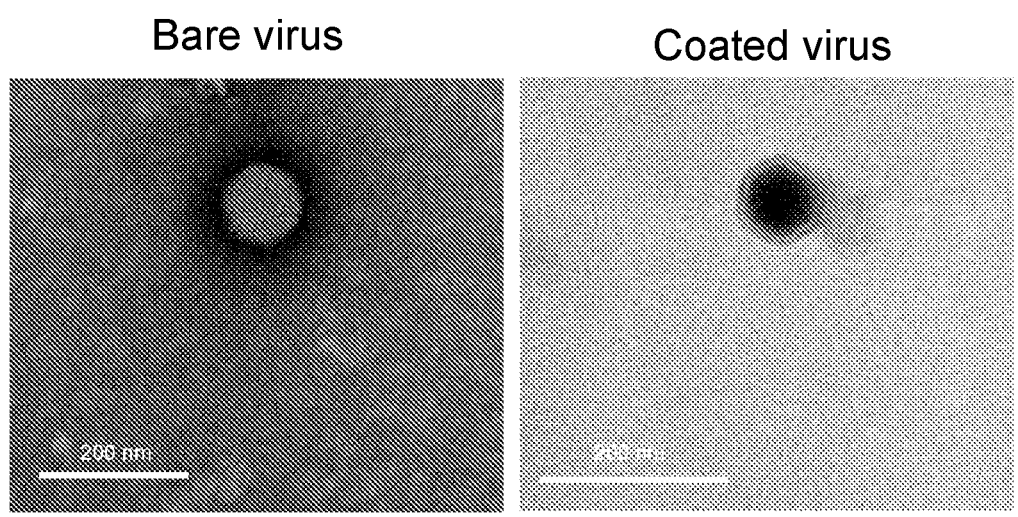
FIG. 3 shows the TEM images of a bare virus and a coated virus.
Figure 4:
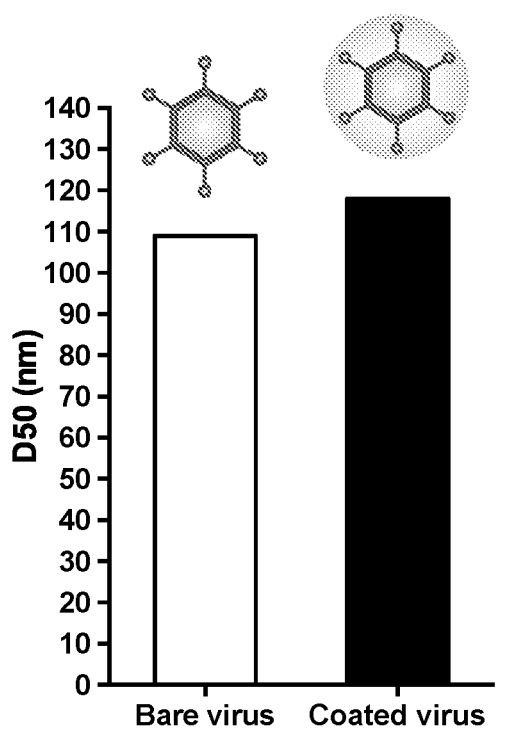
Figure 6:
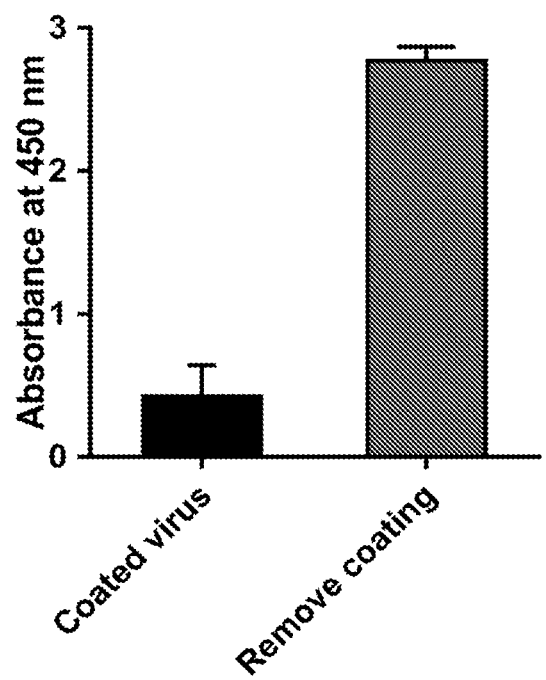

The resulted coated nanoparticles were imaged by Transmission electron microscopy (TEM). FIG. 3 shows the image comparison between the bare virus and RBC membrane coated virus. The particle size comparison is shown in FIG. 4, which suggests the coating layer is about 10 nm. The TEM image show the size of nanoparticles is in a range of 110 nm to 120 nm (about 118 nm).

Figure 5:
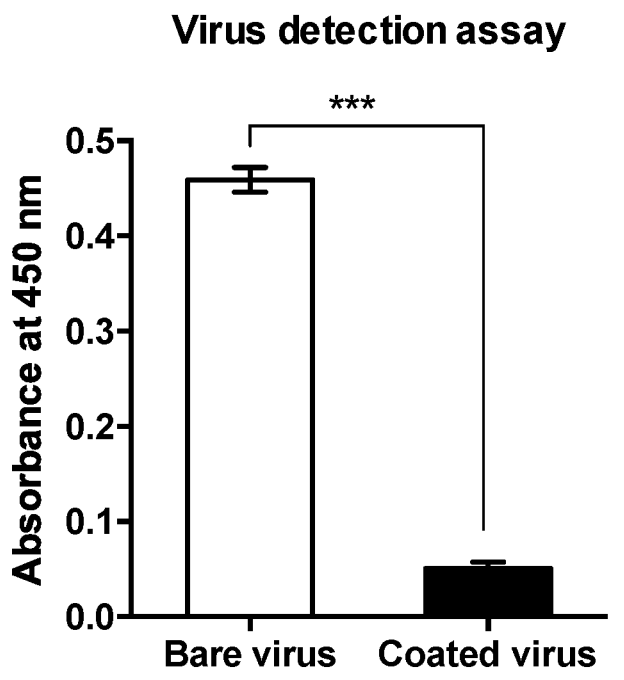

FIG. 5 shows that RBC membrane coated virus was protected from detection antibody while the bare virus was clearly shown; the absorbance difference is very significant indicating the very good RBC membrane coating result. Next the coated nanoparticles went through a process to remove the RBC membrane and then subject to the same ELISA test to further confirm the coating result.

For the coating removal, mix 200 uL of coated virus with 50 uL of sample preparation buffer (Virusys Corporation, contains surfactant) before processing ELISA. FIG. 6 shows that after removal of the RBC membrane, the viruses were detected again, confirming the prior coated viruses.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A process of making a nanoparticle comprising combining an inner core comprising a single virus, and an outer surface comprising a cellular membrane derived from a blood cell, an adipocyte, a stem cell, an endothelial cell, an exosome, a secretory vesicle or a synaptic vesicle in a non-salt water solution; applying sonication to said mixture to form a nanoparticle comprising said inner core coated with said outer surface.

2. The process of claim 1, where said non-salt water solution is a sugar solution.

3. The process of claim 2, wherein said sugar solution is sucrose, or dextrose containing solution.

4. The process of claim 1 wherein said virus is an oncolytic virus.

5. The process of claim 4, wherein said oncolytic virus is herpesvirus; vaccinia virus; reovirus; adenovirus; measles virus, parvovirus, or combinations thereof.

6. The process of claim 4 wherein said virus is adenovirus.

7. The process of claim 1 wherein said blood cell is red blood cell, white blood cell, or platelet.

8. The process of claim 1 wherein said blood cell is red blood cell.

* * * * *